(12) United States Patent
Acklin et al.

(10) Patent No.: US 10,821,286 B2
(45) Date of Patent: Nov. 3, 2020

(54) ELECTRICAL STIMULATOR CONFIGURATION WITH INITIAL HIGH-DENSITY STIMULATION

(71) Applicant: Medtronic, Inc., Minneapolis, MN (US)

(72) Inventors: Brian K. Acklin, Charleston, WV (US); Michael E. Newell, Rapid City, SD (US)

(73) Assignee: Medtronic, Inc., Minneapolis, MN (US)

(*) Notice: Subject to any disclaimer, the term of this patent is extended or adjusted under 35 U.S.C. 154(b) by 97 days.

(21) Appl. No.: 15/874,613

(22) Filed: Jan. 18, 2018

(65) Prior Publication Data

US 2019/0076658 A1 Mar. 14, 2019

Related U.S. Application Data

(60) Provisional application No. 62/556,052, filed on Sep. 8, 2017.

(51) Int. Cl.
*A61N 1/36* (2006.01)
*A61N 1/05* (2006.01)
*A61N 1/372* (2006.01)

(52) U.S. Cl.
CPC ..... *A61N 1/36175* (2013.01); *A61N 1/36062* (2017.08); *A61N 1/36171* (2013.01);
(Continued)

(58) Field of Classification Search
CPC . A61N 1/05; A61N 1/06; A61N 1/372; A61N 1/36; A61N 1/37247; A61N 1/36175; A61N 1/0551; A61N 1/36185; A61N 1/3606; A61N 1/36171; A61N 1/36062; A61N 1/04; A61N 1/0416; A61N 1/0432;
(Continued)

(56) References Cited

U.S. PATENT DOCUMENTS 8,792,988 B2 * 7/2014 Alataris ............. A61N 1/36182
607/46
8,918,184 B1 * 12/2014 Torgerson .......... A61N 1/36185
607/46
(Continued)

FOREIGN PATENT DOCUMENTS

WO 2018067239 A1 4/2018

OTHER PUBLICATIONS

Kapural, MD, PhD, et al., "Comparison of 10-kHZ High-Frequency and Traditional Low-Frequency Spinal Cord Stimulation for the Treatment of Chronic Back and Leg Pain: 24-Month Results from a Multicenter, Randomized, Controlled Pivotal Trial," Research-Human-Clinical Trials, Neurosurgery, Published online: Sep. 6, 2016, 10 pp.

*Primary Examiner* — Catherine M Voorhees
*Assistant Examiner* — Adreanne A. Arnold
(74) *Attorney, Agent, or Firm* — Shumaker & Sieffert, P.A.

(57) ABSTRACT

An example method includes delivering, by an implantable medical device and during a first period of time, high density electrical neurostimulation therapy to a patient using a first set of electrodes of a plurality of electrodes; and delivering, by the implantable medical device and during a second period of time, high density electrical neurostimulation therapy to the patient using a second set of electrodes of the plurality of electrodes.

16 Claims, 6 Drawing Sheets

(52) U.S. Cl.
CPC ..... *A61N 1/36185* (2013.01); *A61N 1/37247* (2013.01); *A61N 1/0551* (2013.01); *A61N 1/36071* (2013.01); *A61N 1/36167* (2013.01)

(58) Field of Classification Search
CPC .... A61N 1/32; A61N 1/0031; A61N 1/36014; A61N 1/36021; A61N 1/0502; A61N 1/0504; A61N 1/36521; A61N 1/36585; A61B 5/04001; A61B 5/6877; A61B 5/6878

See application file for complete search history.

(56) References Cited

U.S. PATENT DOCUMENTS

| | | | | |
|---|---|---|---|---|
| 9,827,421 | B2 * | 11/2017 | Greiner | A61N 1/36071 |
| 2010/0121215 | A1 * | 5/2010 | Giftakis | A61N 1/36082 |
| | | | | 600/544 |
| 2013/0110194 | A1 | 5/2013 | Wei | |
| 2014/0180361 | A1 * | 6/2014 | Burdick | A61N 1/0553 |
| | | | | 607/49 |
| 2014/0296936 | A1 * | 10/2014 | Alataris | A61N 1/36132 |
| | | | | 607/46 |

* cited by examiner

ELECTRICAL STIMULATOR CONFIGURATION WITH INITIAL HIGH-DENSITY STIMULATION

This application claims the benefit of U.S. Provisional Application No. 62/556,052 filed Sep. 8, 2017, the entire content of which is hereby incorporated by reference.

TECHNICAL FIELD

This disclosure generally relates to systems for electrical stimulation of a patient.

BACKGROUND

Medical devices, including implantable medical devices (IMDs), may be used to treat a variety of medical conditions. Medical electrical stimulation devices, for example, may deliver electrical stimulation therapy to a patient via external and/or implanted electrodes. Electrical stimulation therapy may include stimulation of nerve tissue, muscle tissue, the brain, the heart, or other tissue within a patient. In some examples, an electrical stimulation device is fully implanted within the patient. For example, an implantable electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads with percutaneous lead extensions.

Medical electrical stimulators have been proposed for use to relieve a variety of symptoms or conditions such as chronic pain, tremor, Parkinson's disease, depression, epilepsy, migraines, urinary or fecal incontinence, pelvic pain, sexual dysfunction, obesity, and gastroparesis. An electrical stimulator may be configured to deliver electrical stimulation therapy via leads that include electrodes implantable proximate to the spinal cord, gastrointestinal organs, sacral nerve, peripheral nerves, or within the brain of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In one example, a method includes delivering, by an implantable medical device and during a first period of time, high density electrical neurostimulation therapy to a patient using a first set of electrodes of a plurality of electrodes; and delivering, by the implantable medical device and during a second period of time, high density electrical neurostimulation therapy to the patient using a second set of electrodes of the plurality of electrodes.

In another example, an electrical neurostimulation therapy system includes a plurality of electrodes disposed along a lead inserted proximal to a spinal cord of a patient, the lead connected to an electrical neurostimulation therapy device; and a stimulation generator configured to: deliver high density electrical stimulation via a first set of the plurality of electrodes during a first period of time; and deliver high density electrical stimulation via a second set of the plurality of electrodes during a second period of time.

In another example, an electrical neurostimulation therapy system includes means for delivering, during a first period of time, high density electrical neurostimulation therapy to a patient using a first set of electrodes of a plurality of electrodes; and means for delivering, during a second period of time, high density electrical neurostimulation therapy to the patient using a second set of electrodes of the plurality of electrodes.

In another example, a non-transitory computer readable storage medium stores instructions that, when executed, cause a stimulation generator of an implantable medical device to deliver, during a first period of time, high density electrical neurostimulation therapy to a patient using a first set of electrodes of a plurality of electrodes; and deliver, during a second period of time that is after the first period of time, high density electrical neurostimulation therapy to the patient using a second set of electrodes of the plurality of electrodes.

In another example, a method includes delivering, by an implantable medical device and during a first period of time, high density electrical neurostimulation therapy to a patient using a first set of electrodes of a plurality of electrodes; and delivering, by the implantable medical device and during a second period of time that is after the first period of time, low density electrical neurostimulation therapy to the patient using a second set of electrodes of the plurality of electrodes.

In another example, an electrical neurostimulation therapy system includes a plurality of electrodes disposed along a lead inserted proximal to a spinal cord of a patient, the lead connected to an electrical neurostimulation therapy device; and a stimulation generator configured to: deliver high density electrical stimulation via a first set of the plurality of electrodes during a first period of time; and deliver low density electrical stimulation via a second set of the plurality of electrodes during a second period of time that is after the first period of time.

In another example, an electrical neurostimulation therapy system includes means for delivering, during a first period of time, high density electrical neurostimulation therapy to a patient using a first set of electrodes of a plurality of electrodes; and means for delivering, during a second period of time that is after the first period of time, low density electrical neurostimulation therapy to the patient using a second set of electrodes of the plurality of electrodes.

In another example, a non-transitory computer readable storage medium stores instructions that, when executed, cause a stimulation generator of an implantable medical device to deliver, during a first period of time, high density electrical neurostimulation therapy to a patient using a first set of electrodes of a plurality of electrodes; and deliver, during a second period of time that is after the first period of time, low density electrical neurostimulation therapy to the patient using a second set of electrodes of the plurality of electrodes.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
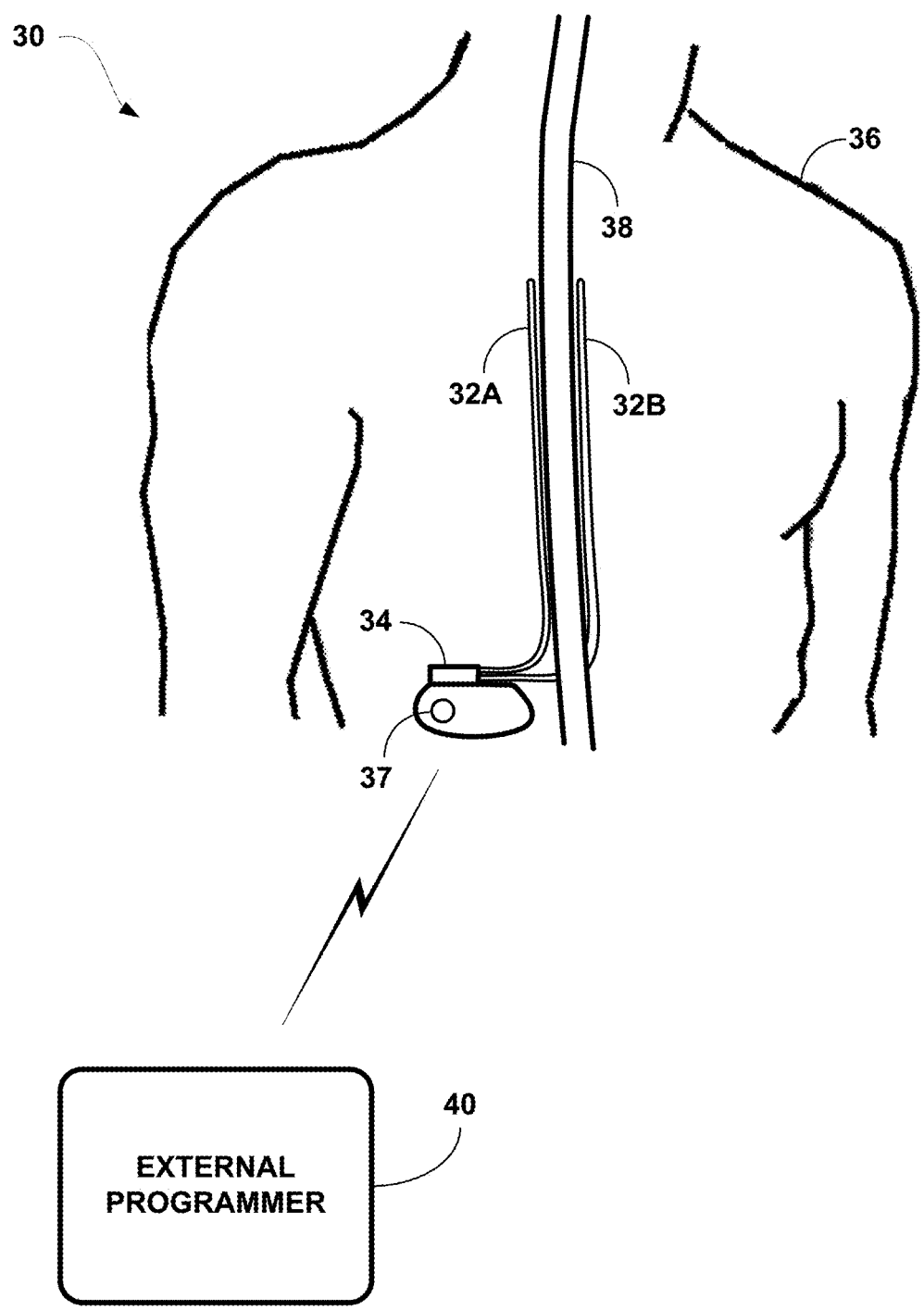
FIG. 1 is a conceptual diagram illustrating an example system that delivers stimulation therapy to a spinal cord of a patient in accordance with the techniques of the disclosure.

In general, this disclosure describes devices, systems, and techniques for utilizing high density electrical neurostimulation to treat patients. Neurostimulators may be configured to deliver stimulation with various parameters. For instance, neurostimulators may be configured to deliver high density (HD) stimulation and/or low density (LD) stimulation. HD stimulation may be stimulation in which pulses are delivered with a duty cycle greater than a threshold duty cycle (e.g., a duty cycle of greater than approximately 5%). For example, if the threshold duty cycle is 5%, stimulation in which pulses are delivered at a frequency of 1000 Hz with a pulse width of 90 microseconds may be considered HD stimulation because the resulting duty cycle is greater than approximately 5% (i.e., 1000 Hz*90 microseconds=9% duty cycle). LD stimulation may be stimulation in-which pulses are delivered with a duty cycle less than the threshold duty cycle. For example, if the threshold duty cycle is approximately 5%, stimulation in which pulses are delivered at a frequency of 40 Hz with a pulse width of 450 microseconds may be considered LD stimulation because the resulting duty cycle is less than 5% (i.e., 40 Hz*450 microseconds=2% duty cycle).

In general, to be effective, LD stimulation may require stimulation intensities (e.g., pulse amplitudes) that are greater than intensities used for HD stimulation. LD stimulation may require an initial characterization of the neurostimulator (e.g., paresthesia mapping). For instance, when a patient receives a neurostimulator (e.g., the patient has a neurostimulator implanted in the patient's body), a practitioner may start with a particular setting (e.g., a particular electrode configuration), increase stimulation intensity until an effect of the stimulation (e.g., paresthesia or pain relief) is perceptible to the patient, and ask the patient where they feel the stimulation (sensation or paresthesia over the top, or in the vicinity, of where the patient's pain is felt, e.g., left leg, lower back). This feedback may allow the practitioner to determine whether or not a lead of the neurostimulator is in a correct or an incorrect position to achieve therapeutic efficacy. Additionally or alternatively, the practitioner utilize fluoroscopic imaging to verify lead placement. In some examples, the initial characterization and/or the fluoroscopic imaging may allow a practitioner to determine which electrodes of the lead are in a T9-T10 disk space of the patient's spine.

The effects of LD stimulation may be quickly perceived by the patient. For instance, it may take less than a minute from the time the neurostimulator begins delivering LD stimulation until the patient starts to feel the effects. As such, it is possible for many different settings to be trialed during the initial characterization procedure.

As stated above, to be effective, LD stimulation may require stimulation intensities that are greater than HD stimulation intensities. Put the other way, HD stimulation may be effective (e.g., at providing patients relief from pain) with stimulation intensities that are lesser than the intensities of the LD stimulation required for therapeutic results. However, as opposed to LD stimulation where the effects of the stimulation are felt almost instantly, patients may take longer to feel the effects of HD stimulation. Due to the delay in feeling the effects of HD stimulation, it may not be possible to determine if HD stimulation is effective during an initial characterization procedure. As such, many practitioners and patients may not utilize HD stimulation.

In accordance with one or more techniques of this disclosure, a neurostimulator may be initially configured to deliver stimulation in a plurality of phases. In a first phase, referred to as a first HD phase, the neurostimulator may deliver HD stimulation for a first period of time that is selected to be long enough for a patient to feel the effects of the HD stimulation (e.g., at least 24 hours, at least 48 hours, etc.). For example, the neurostimulator may deliver pulses of electrical stimulation at greater than or equal to approximately 1000 Hz with a pulse width of greater than or equal to 90 microseconds via a first set of electrodes of a plurality of electrodes coupled to the neurostimulator. In some examples, the frequency of pulse delivery may greater than 800 Hz, for example, greater than 1000 Hz, and the pulse width may be less than 100 microseconds, for example, less than 90 microseconds.

In some examples, the amplitude of the electrical stimulation signal is selected such that a stimulation intensity level of the electrical stimulation signal is less than a perception or paresthesia threshold intensity level for the patient. Stimulation delivered at an intensity that may be less than a perception or paresthesia threshold intensity level for the patient may be referred to as sub-threshold stimulation. The perception threshold may be the lowest level of electrical stimulation that is sufficient for the patient to perceive that the IMD is delivering electrical stimulation. The paresthesia threshold may be the lowest level of electrical stimulation that causes paresthesia in the patient. Paresthesia may cause discomfort in the patient, and is sometimes described as a "pins and needles" sensation. A clinician and/or the patient may select an amplitude, and titrate the amplitude until the electrical stimulation therapy is less than a perception or paresthesia threshold intensity level for the patient. In one non-limiting example, the electrical stimulation signal has a current amplitude in a range of 0.1 microamps to 100 milliamps. In another non-limiting example, the amplitude may be selected to be in a range of about 0.1 milliamps to about 25.5 milliamps, such as in a range of about 0.5 milliamps to about 5 milliamps. In another non-limiting example, the electrical stimulation signal has a voltage amplitude in a range of 10 millivolts to 14 Volts. In another non-limiting example, the electrical stimulation signal has a voltage amplitude in a range of 50 millivolts to 14 Volts, such as in a range of about 500 millivolts to about 5 Volts. When controlled by the patient, the amplitude may be constrained within a range set by a clinician (e.g., which may be narrower than the range of amplitudes available to the clinician).

The first set of electrodes may include a first electrode of the plurality of electrodes that is implanted over a midline of a T9-T10 disk space of the patient, and a second electrode of the plurality of electrodes that is immediately superior (i.e., cranial) to the first electrode. In some examples, the first electrode may be configured as a cathode and the second electrode may be configured as an anode.

During the first phase, e.g., with a duration of greater than or equal to approximately 24 hours, and in some examples with a duration of greater than or equal to approximately 48 hours, the stimulation parameters may be kept relatively constant. However, the patient may be provided with the ability to adjust an intensity/amplitude of the HD stimulation. For instance, the patient or the clinician may use a programmer (e.g., a clinician programmer or a patient programmer) to adjust the intensity/amplitude of the HD stimulation to a level at which the patient is still comfortable (e.g., titrate the intensity/amplitude). For instance, the clinician may increase the intensity to patient perception (e.g., in 0.3 volt to 0.5 volt intervals), waiting a few seconds before increase. However, as stated above, the HD stimulation may not immediately (e.g., instantly) provide pain relief. As such, the patient and/or clinician may give the HD stimulation some time (e.g., 24 hours, 48 hours, etc.) to become effective before changing the settings (e.g., before transitioning to a second phase).

During the first HD phase, the stimulation parameters (e.g., the frequency, pulse width, and electrode selections) may be fixed and/or kept relatively constant. However, in some examples, the patient or the clinician may use a programmer (e.g., a clinician programmer or a patient programmer) to adjust the intensity/amplitude of the HD stimulation.

After the first HD phase, the patient may be queried as to whether the stimulation is effective (e.g., whether their pain has been substantially reduced). If the HD stimulation is effective, the neurostimulator may continue to deliver the HD stimulation. However, if the HD stimulation is not effective, a second phase may begin in which the delivery of the stimulation is modified. In the second phase, referred to as a second HD phase, the neurostimulator may deliver HD stimulation via a second (different) set of electrodes for a second period of time (e.g., a period of time that is selected to be long enough for a patient to feel the effects of the modified HD stimulation). In some examples, the second period of time for the second HD phase may be greater than or equal to approximately 48 hours. The second set of electrodes may include the second electrode (i.e., the electrode of the plurality of electrodes that is immediately superior to the first electrode that is implanted over the midline of the T9-T10 disk space of the patient), and a third electrode of the plurality of electrodes that is immediately superior to the second electrode. In some examples, other than using a different set of electrodes, the stimulation parameters may be the same as the initial HD stimulation. For instance, the neurostimulator may deliver pulses of electrical stimulation at greater than or equal to approximately 1000 Hz with a pulse width of greater than or equal to approximately 90 microseconds via the second set of electrodes.

During the second phase, the stimulation parameters (e.g., the frequency, pulse width, and electrode selections) may be fixed and/or kept relatively constant. However, patient 36 may be provided with the ability to adjust a current or voltage pulse amplitude of the HD stimulation. For instance, the patient may use a programmer to adjust the intensity/amplitude of the HD stimulation.

After the second HD phase, the patient may be queried as to whether the modified stimulation delivered in the second HD phase is effective (e.g., whether their pain has been substantially reduced). If the modified HD stimulation is effective, the neurostimulator may continue to deliver the modified HD stimulation. However, if the modified HD stimulation is not effective, a third phase may begin in which the delivery of the stimulation may be again modified. In the third phase, referred to as a low density (LD) phase, the neurostimulator may switch to delivering LD stimulation for a third period of time. The neurostimulator may deliver the LD stimulation using parameters identified during the initial characterization procedure (e.g., stimulation with pulses delivered at 40 Hz with pulse widths of 450 microseconds). In some examples, the LD phase may be immediately after the first HD phase. For instance, if the HD stimulation in a first HD phase is not effective, the neurostimulator may move to a LD phase without performing a second HD phase.

By using the above-described procedure in which HD stimulation is utilized first, patients may be provided with a more simplistic experience on the day that the stimulator is implanted. For instance, by using a constant starting parameter (e.g., 1000 Hz frequency with 90 microsecond pulse width) and common spinal target (i.e., midline of T9-T10 disk space), patients may avoid more complicated and time-intensive configurations either indefinitely (if HD stimulation is effective) or at least avoid the more complex configurations on the day of implantation. Additionally, performing the mapping operations with the patient (during the characterization procedure) may cause the patient to focus on location of perception as opposed to overall effectiveness of the treatment. As such, by performing one or more HD phases prior to performing the LD phase, the patient's focus may be taken off of location, which may promote evaluation of overall pain rather than location of effect.

In some examples, the neurostimulator may switch to the LD phase if the stimulation in the first HD phase is not effective (i.e., the second HD phase may be skipped). In other examples, one or more additional HD phases may be added between the second HD phase and the LD phase.

While described as being of the same length of time, the various phases may be of the same of different lengths. As one example, the first HD phase may be greater than or equal to approximately 48 hours long (e.g., 48 hours) while the second HD phase may be greater than or equal to approximately 24 hours long (e.g., 24 hours). As another example, the first HD phase and the second HD phase may each be at approximately the same length, e.g., greater than or equal to approximately 48 hours for the first HD phase and greater than or equal to approximately 48 hours for the second HD phase.

As described above, the density of stimulation may represent how often the stimulation is delivered. For instance, stimulation density may be determined based on a frequency at which stimulation pulses and a width of the stimulation pulses. However, density may be different than dose. For instance, in addition to frequency and pulse width, stimulation dose may be further based on the amplitude of the pulses. As such, stimulation dose may describe "how much" therapy is being delivered.

FIG. 1 is a conceptual diagram illustrating system 30 that delivers stimulation therapy to spinal cord 38 of patient 36 in accordance with the techniques of the disclosure. System 30 delivers electrical neurostimulation therapy from implantable stimulator 34 to spinal cord 38 via one or more electrodes (not shown) carried by, i.e., located on, implantable medical leads 32A and 32B (collectively "leads 32") as well as the housing of implantable stimulator 34, e.g., housing electrode 37. System 30 and, more particularly, implantable stimulator 34, may operate in in a current-based or voltage-based configuration. That is, in a current-based example, implantable stimulator 34 delivers controlled current stimulation pulses or waveforms to patient 6 via one or more regulated, stimulation electrodes. Alternatively, in a voltage-based example, implantable stimulator 34 may be configured to deliver constant voltage pulses. Various parameters of the pulses or waveforms may be defined by one or more stimulation programs. The pulses or waveforms may be delivered substantially continuously or in bursts, segments, or patterns, and may be delivered alone or in combination with pulses or waveforms defined by one or more other stimulation programs. In some example, implantable stimulator 34 delivers spinal cord stimulation (SCS) therapy to patient 6 via the electrodes carried by, i.e., located on, leads 32 to provide pain relief therapy to patient 6.

Stimulator 34 may be implanted in patient 36 at a location minimally noticeable to the patient. For SCS, stimulator 34 may be located in the lower abdomen, lower back, or other location to secure the stimulator. Leads 32 may be tunneled from stimulator 34 through tissue to reach the target tissue adjacent to spinal cord 38 for stimulation delivery. At the distal ends of leads 32 are one or more electrodes (not shown) that transfer the stimulation pulses from the lead to the tissue substantially simultaneously with stimulation pulses.

In the example of FIG. 1, the distal ends of leads 32 are placed adjacent to the target tissue of spinal cord 38. The proximal ends of leads 32 may be both electrically and mechanically coupled to implantable stimulator 34 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing.

Application of certain techniques will be described in this disclosure with respect to implantable stimulator 34 and implantable leads 32 having ring electrodes for purposes of illustration. Ring electrodes are commonly used in electrical neurostimulation applications because they are simple to program and are capable of delivering an electrical field to any tissue adjacent to leads 32. However, other types of electrodes may be used. For example, the electrodes of leads 32 may have a complex electrode array geometry that is capable of producing shaped electrical fields. The complex electrode array geometry may include multiple electrodes (e.g., partial ring or segmented electrodes) around the perimeter of each lead 32, rather than one ring electrode. In this manner, electrical stimulation may be directed in a specific direction from leads 32 to enhance therapy efficacy and reduce possible adverse side effects from stimulating a large volume of tissue. In alternative examples, leads 32 may have shapes other than elongated cylinders as shown in FIG. 1. For example, leads 32 may be electrode pads on a paddle lead, circular (i.e., ring) electrodes surrounding the body of leads 32, spherical leads, bendable leads, conformable electrodes, cuff electrodes, segmented electrodes, or any other type of electrodes capable of forming unipolar, bipolar or multi-polar electrode configurations and effective in treating patient 6. In some examples, one or more of the electrodes may be unregulated. In some examples, the housing of implantable stimulator 34, e.g., housing electrode 37, functions as an anode and/or return path for the electrical stimulation.

The stimulation pulses may be delivered using various electrode arrangements such as unipolar arrangements, bipolar arrangements or multipolar arrangements. A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of more than one anode on a lead that each source current and one or more cathodes on the same lead or another lead that sink current, or the use of one anode on a lead that sources current and multiple cathodes on the same lead or another lead that sink current. A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver electrical stimulation in accordance with techniques described in this disclosure.

Implantable stimulator 34 delivers stimulation to spinal cord 38 to reduce the amount of pain perceived by patient 36. The stimulation delivered by implantable stimulator 34 may take the form of stimulation pulses, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 34 perceives the interruption of pain signals as a reduction in pain and, therefore, efficacious therapy.

In some examples, therapy system 30 further includes external programmer 40. External programmer 40 may be used to define stimulation therapy parameters for use by implantable stimulator 34. In some examples, programmer 40 is a clinician programmer, which is a handheld computing device that permits a clinician to program stimulation therapy for patient 6 via a user interface, e.g., using input keys and a display. For example, using the clinician programmer, the clinician may specify stimulation parameters, i.e., create programs, for use in delivery of stimulation therapy. The clinician programmer may support telemetry (e.g., radio frequency (RF) telemetry) with implantable stimulator 34 to download programs and, optionally, upload operational or physiological data stored by implantable stimulator 34. In this manner, the clinician may periodically interrogate implantable stimulator 34 to evaluate efficacy and, if necessary, modify the programs or create new programs. In some examples, the clinician programmer transmits programs to a patient programmer (not depicted) in addition to or instead of implantable stimulator 34. In some examples, the patient programmer may serve as the clinician programmer.

In other examples, external programmer 40 is a patient programmer. Like the clinician programmer, the patient programmer may be a handheld computing device. The patient programmer may also include a display and input keys to allow patient 36 to interact with the patient programmer and implantable stimulator 34. In this manner, the patient programmer provides patient 36 with a user interface for control of the stimulation therapy delivered by implantable stimulator 34. For example, patient 36 may use the patient programmer to start, stop or adjust electrical stimulation therapy. In particular, the patient programmer may permit patient 36 to adjust stimulation parameters of a program such as duration, current or voltage amplitude, pulse width and pulse rate. Patient 36 may also select a program, e.g., from among a plurality of stored programs, as the present program to control delivery of stimulation by implantable stimulator 34.

With reference to FIG. 1, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry. In accordance with this disclosure, programmer 40 may transmit to the stimulator 34 information regarding the patient and regarding therapy the patient received during previous sessions including, for example, images that show placement of leads 32.

Whether programmer 40 is configured for clinician or patient use, programmer 40 may communicate to implantable stimulator 34 or any other computing device via wireless communication. Programmer 40, for example, may communicate via wireless communication with implantable stimulator 34 using radio frequency (RF) telemetry techniques known in the art or other communication standards such as, for example, Bluetooth®. Programmer 40 may also communicate with another programmer or computing device via a wired or wireless connection using any of a variety of local wireless communication techniques, such as RF communication according to the 802.11 or Bluetooth® specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with implantable stimulator 34 and other programming devices via remote telemetry techniques known in the art, communicating via a local area network (LAN), wide area network (WAN), public switched telephone network (PSTN), or cellular telephone network, for example.

Implantable stimulator 34, and external programmer 40 may communicate via cables or a wireless communication, as shown in FIG. 1. External programmer 40 may, for example, communicate via wireless communication with implantable stimulator 4 using RF telemetry techniques known in the art or other standard communication protocols such as, for example, Bluetooth®. External programmer 40 also may communicate with each other using any of a variety of wireless communication techniques, such as RF communication according to the 802.11 or Bluetooth® specification sets, infrared communication, e.g., according to the IrDA standard, or other standard or proprietary telemetry protocols. External programmer 40 may include a transceiver to permit bi-directional communication with implantable stimulator 34.

According to the techniques of the disclosure, a clinician implants one or more leads 32 proximal to spinal cord 38 of patient 36. In some examples, the clinician may implant at least one lead 32 at an angle relative to and across an anatomical midline of spinal cord 38 of patient 36. In some examples, the at least one lead 32 is implanted at an angle of 5-20 degrees relative to the anatomical midline of spinal cord 38 of patient 36. In some examples of the techniques disclosed herein, the clinician implants a first lead 32A and second lead 32B, both coupled to stimulator 34, at angles of approximately 5 to 20 degrees relative to and across the anatomical midline of spinal cord 38. In alternate examples, the first lead 32A is implanted parallel to and offset from the anatomical midline of spinal cord 38, while the second lead 32B is implanted at an angle of approximately 5 to 20 degrees relative to and across the anatomical midline of spinal cord 38. Such an implantation procedure as described herein may ensure that at least several electrodes are implanted on either side of the physiological midline of spinal cord 38.

Figure 5A:
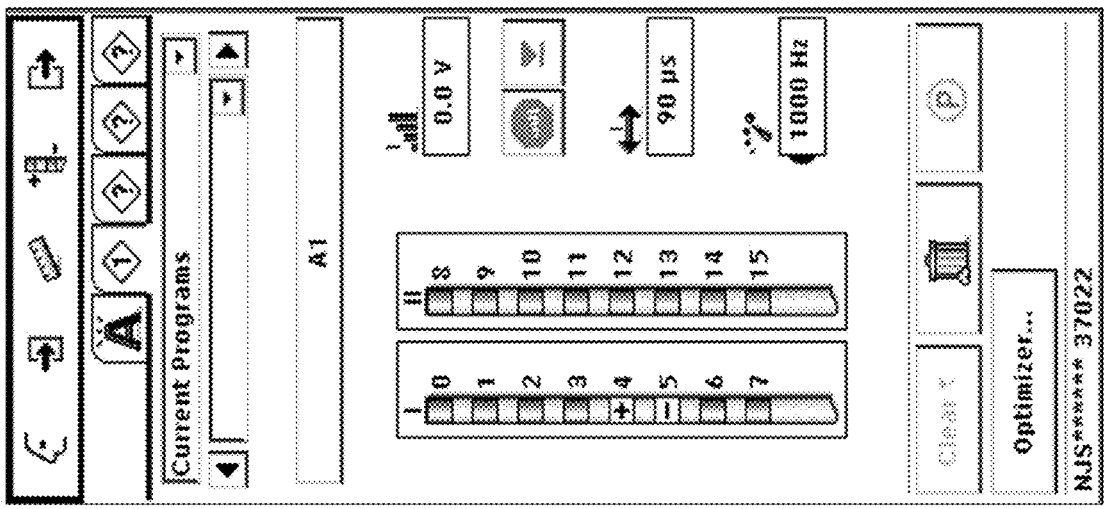
FIGS. 5A-5C illustrate exemplary screen shots of a display on a user interface of an external programmer, in accordance with the techniques of the disclosure.

After surgical implantation of stimulator 34, the clinician may perform an initial characterization procedure. For instance, the clinician may test various combinations of electrodes to determine the combination that provides the greatest pain relief to the patient using LD stimulation. The clinician may use programmer 40 to program stimulator 34 to deliver, during a first period of time (e.g., a first HD phase), high density (HD) electrical neurostimulation therapy to patient 36 using a first set of electrodes of a plurality of electrodes positioned on leads 32. The first set of electrodes may include a first electrode of the plurality of electrodes that is implanted over a midline of a T9-T10 disk space of patient 36, and a second electrode of the plurality of electrodes that is immediately superior to the first electrode. As discussed above, the clinician may determine which electrodes of the plurality of electrodes are implanted over a midline of a T9-T10 disk space of patient 36 during the initial characterization procedure (e.g., during paresthesia mapping) and/or with fluoroscopic imaging. In one particular example, the clinician may program stimulator 34 using programmer 40 with the settings illustrated in FIG. 5A. As discussed above, the first period of time may be at least 24 hours, at least 48 hours, or longer.

After the first period of time has expired, patient 36 may be asked whether the stimulation is effective. As one example, the clinician may verbally ask patient 36 whether the stimulation is effective, and receive a verbal reply from the patient. As another example, a clinician or patient programmer or other device may automatically present the question to patient 36, and receive a reply by user input on the programmer or device.

Figure 5B:
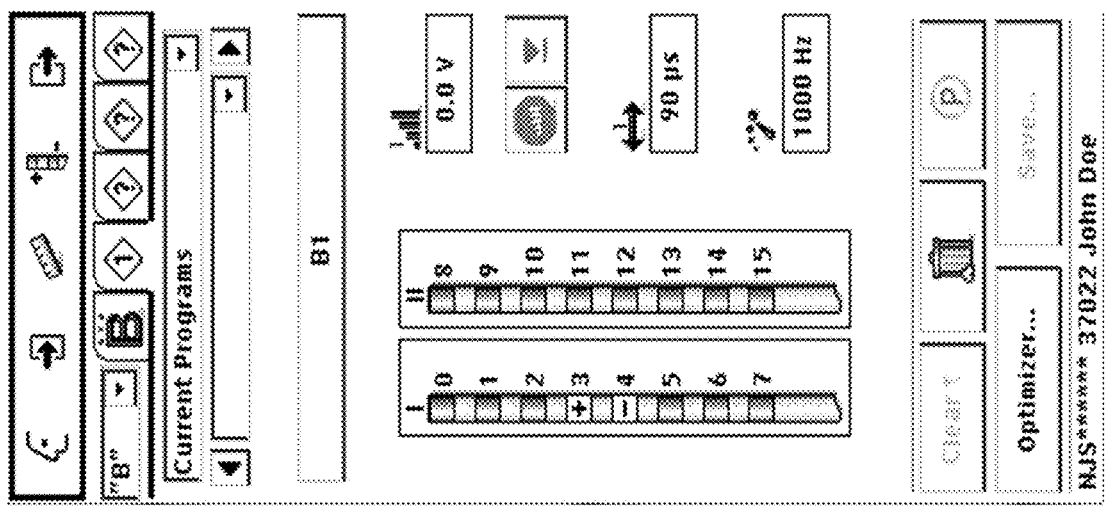

If patient 36 states that the stimulation is not effective, stimulator 34 may be programmed to deliver, during a second period of time (e.g., a second HD phase), high density electrical neurostimulation therapy to patient 36 using a second set of electrodes of the plurality of electrodes. The second set of electrodes may include the second electrode and a third electrode of the plurality of electrodes that is immediately superior to the second electrode. As one example, the clinician may use programmer 40 to program stimulator 34 with the settings illustrated in FIG. 5B. As another example, stimulator 34 may automatically transition to stimulating using the settings illustrated in FIG. 5B in response to the patient providing user input to the patient programmer or other device indicating that the stimulation during the first period of time is not effective.

After the second period of time, patient 36 may be asked whether the stimulation is effective. As one example, the clinician may verbally ask patient 36 whether the stimulation is effective, and receive a verbal reply from the patient. As another example, a clinician or patient programmer or other device may automatically present the question to patient 36, and receive a reply by user input on the programmer or device.

Figure 5C:
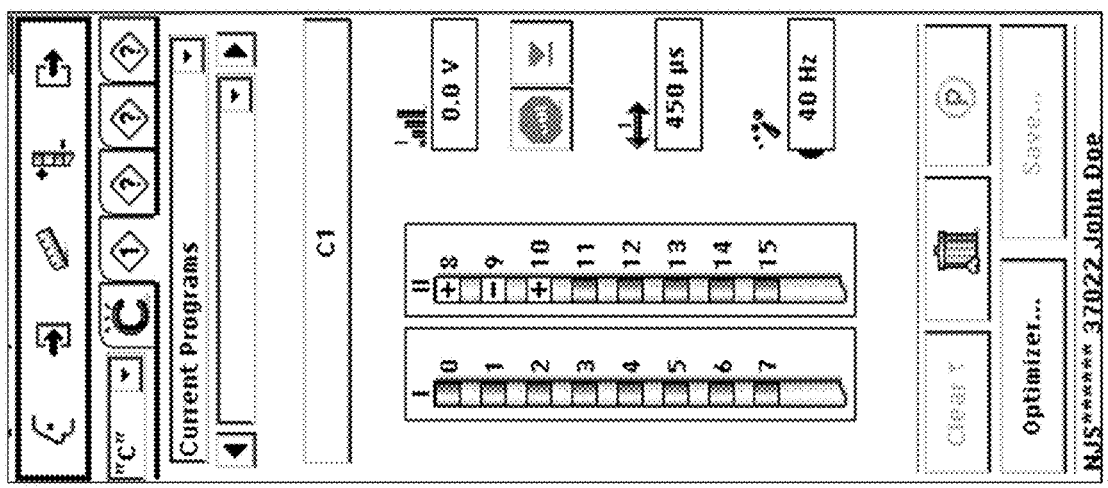

If patient 36 states that the stimulation is not effective, stimulator 34 may be programmed to deliver, during a third period of time (e.g., a LD phase), low density electrical neurostimulation therapy to patient 36 using a third set of electrodes of the plurality of electrodes. As one example, the clinician may use programmer 40 to program stimulator 34 with the settings illustrated in FIG. 5C. As another example, stimulator 34 may automatically transition to stimulating using the settings illustrated in FIG. 5C in response to the patient providing user input to the patient programmer or other device indicating that the stimulation during the second period of time is not effective.

In some examples, patient 36 may leave a clinic at which stimulator 34 was implanted/where the stimulator was programmed during the first HD phase (e.g., patient 36 may go home). Patient 36 may periodically check-in (e.g., daily) with the clinician or other representative of the clinician during the first HD phase and any subsequent phases. In some examples, patient 36 may return to the clinic at the end of a phase (e.g., at the end of the first HD phase, before stimulator 34 transitions to delivering HD stimulation via the second set of electrodes in the second HD phase). In other examples, patient 36 may not return to the clinic at the end of a phase.

At the end of any particular phase, patient 36 and/or the clinician may determine that the settings used during the particular phase are effective. In such case, patient 36 and/or the clinician may program stimulator 34 to continue delivering stimulation using the settings used during the particular phase (e.g., to perform chronic/long term stimulation).

Figure 2:
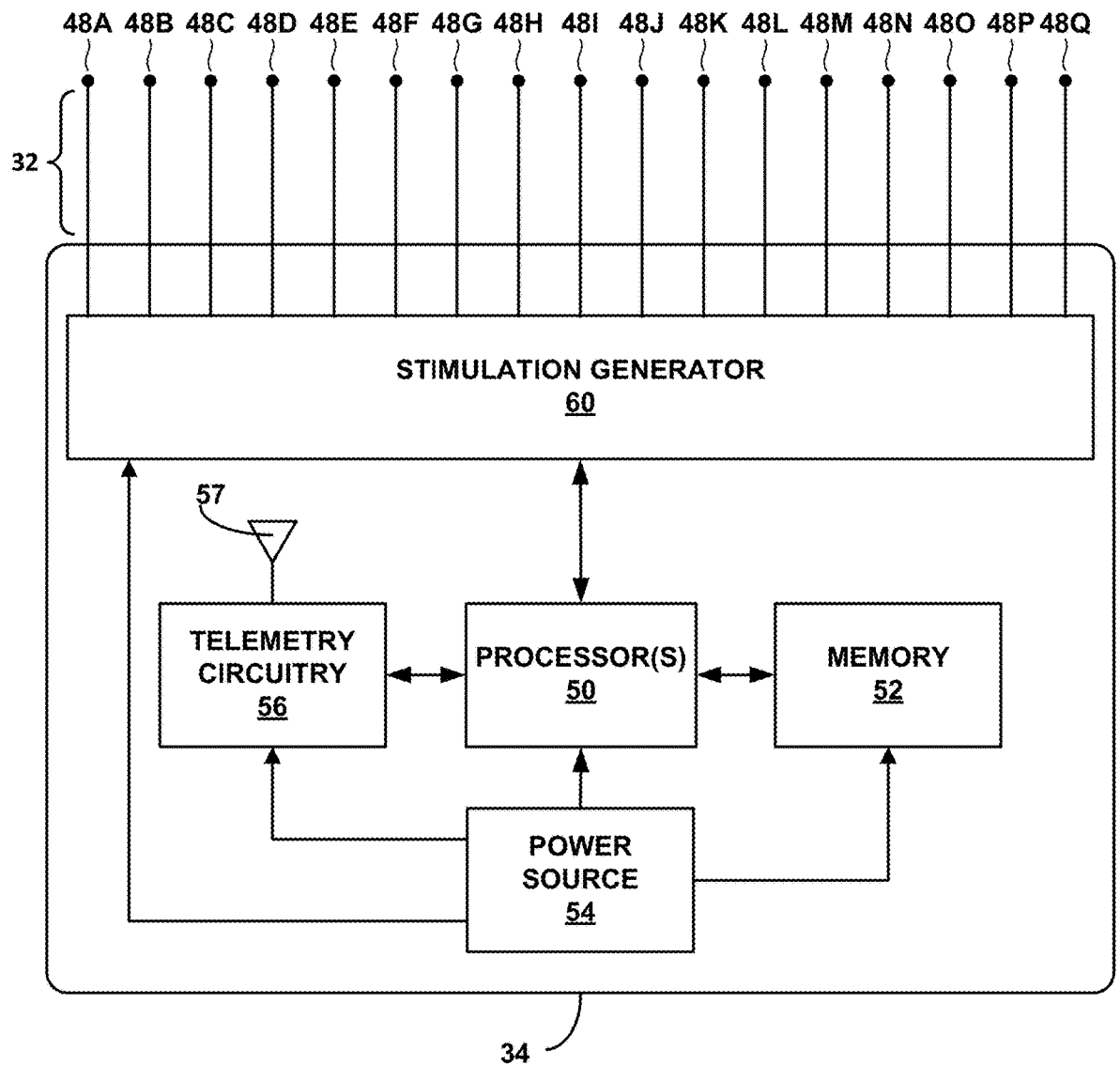
FIG. 2 is a block diagram illustrating various example components of an implantable electrical stimulator of a system in accordance with the techniques of the disclosure.

FIG. 2 is a block diagram illustrating various components of an example implantable stimulator 34 of system 2 in accordance with the techniques of the disclosure. In the example of FIG. 2, implantable stimulator 34 includes processor 50, memory 52, power source 54, telemetry circuitry 56, antenna 57, and a stimulation generator 60. Implantable stimulator 34 is also shown in FIG. 2 coupled to electrodes 48A-Q (collectively "electrodes 48"). Electrodes 48A-48P are implantable and may be deployed on one or more implantable leads 32. With respect to FIG. 1, lead 32A and 32B may carry electrodes 48A-H and electrodes 48I-P, respectively. In some cases, one or more additional electrodes may be located on or within the housing of implantable stimulator 34, e.g., to provide a common or ground electrode or a housing anode. With respect to FIG. 2, leads 32A and 32B may carry electrodes 48A-H and electrodes 48I-P, respectively. In the examples of FIGS. 1 and 2, a lead or lead segment carries eight electrodes to provide a 2×8 electrode configuration (two leads with 8 electrodes each), providing a total of sixteen different electrodes. The leads may be detachable from a housing associated with implantable stimulator 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), two or more leads with 11 or 13 electrodes, or other configurations. Different electrodes are selected to form electrode combinations. Polarities are assigned to the selected electrodes to designate the electrodes as anodes or cathodes and form electrode configurations.

Electrode 48Q represents one or more electrodes that may be carried on a housing, i.e., can, of implantable stimulator 34, e.g., housing electrode 37 of FIG. 1. Electrode 48Q may also be a dedicated short lead extending from the housing, or a proximal portion of one of the leads carrying electrodes 48A-48P. The proximal portion may be closely adjacent to the housing, e.g., at or near a point at which a lead is coupled to the housing, such as adjacent to a lead connection header 8 of the housing. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 4, such as stimulation generator 60, processor 50, memory 52, telemetry circuitry 56, and power source 54.

Housing electrode 48Q may be configured for use as an anode to source current substantially simultaneously with one or more electrodes 48A-48P configured for use as cathodes sinking current in a unipolar arrangement. Housing electrode 48Q may be configured for use as an anode to source current substantially simultaneously with current sourced by another electrode 48A-48P configured for use as an anode in an omnipolar arrangement. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 4, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program group, processor 50 may control stimulation generator 60 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. The electrode combination may include at least one anode on the housing of the IMD, e.g., electrode 48Q, at least one anode on a lead, electrode 48A, and at least one cathode on a lead. The lead-borne anode and cathode may be on the same lead or different leads, if more than one lead is provided. A program may be defined directly, by selecting parameters and electrodes, or by zone-based programming, in which parameters and electrodes are automatically determined by the programmer in response to manipulation or positioning of stimulation zones.

Stimulation generator 60 is electrically coupled to electrodes 48A-P via conductors of the respective lead, such as lead 12 in FIG. 1 or leads 32 in FIG. 2, in implementations in which electrodes 48A-P are carried by, located on, leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 2). Housing electrode 48Q may be configured as a regulated or unregulated electrode to form an electrode configuration in conjunction with one or more of electrodes 48A-48P located on leads of the IMD. Housing electrode 48Q may be configured for use as an anode to source current substantially simultaneously with one or more electrodes, e.g., any of electrodes 48A-48P, on one or more leads configured for use as anodes.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

In one example implementation, e.g., an omnipolar arrangement, stimulation generator 60 may be configured to deliver stimulation using one or more of electrodes 48A-P as stimulation electrodes, e.g., anodes, while substantially simultaneously delivering stimulation using housing electrode 48Q as a stimulation electrode, e.g., anode. The anodes on the lead(s) and the housing may be used to deliver stimulation in conjunction with one or more cathodes on the lead(s). As one illustration, an electrode combination selected for delivery of stimulation current may comprise an anode on the IMD housing, and anode on a lead, and a cathode on the same lead or a different lead. In other examples, the electrode combination may include multiple anodes and/or multiple cathodes on one or more leads in conjunction with at least one anode on the IMD housing. In some examples, the electrode combination may include one or more anodes on one or more leads, and one or more cathodes on the same lead or a different lead, e.g., a bipolar/multipolar arrangement. In other examples, the electrode combination may include an anode on the housing, and one or more cathodes on one or more leads, e.g., omnipolar arrangement. In yet another example, the electrode combination may include a cathode on the housing, and one or more additional cathodes on one or more leads, along with one or more anodes also on the leads, e.g., a variation of an omnipolar arrangement.

In some examples, stimulation generator 60 may include a single source (e.g., voltage or current) or multiple sources that are multiplexed across selected electrodes to provide current or voltage pulses. In some examples, stimulation generator 60 may include a dedicated source and sink for each electrode that is individually controllable.

Telemetry circuitry 56 may include a radio frequency (RF) transceiver to permit bi-directional communication between implantable stimulator 4 and each of clinician programmer 20 and patient programmer 22. Telemetry circuitry 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 4 or take the form of a circuit trace on the circuit board. In this way, telemetry circuitry 56 may permit communication with clinician programmer 40 and patient programmer 22 in FIG. 1 or external programmer 40 in FIG. 2, to receive, for example, new programs or program groups, or adjustments to programs or program groups.

Power source 54 may be a non-rechargeable primary cell battery or a rechargeable battery and may be coupled to power circuitry. However, the disclosure is not limited to implementations in which the power source is a battery. In another example, as an example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional embodiments, power source 54 may include a small rechargeable circuit and a power generation circuit to produce the operating power. Recharging may be accomplished through proximal inductive interaction between an external charger and an inductive charging coil within stimulator 34. In some embodiments, power requirements may be small enough to allow stimulator 34 to utilize patient motion at least in part and implement a kinetic energy-scavenging device to trickle charge a rechargeable battery. A voltage regulator may generate one or more regulated voltages using the battery power.

After surgical implantation of stimulator 34, the clinician may program stimulator 34 with a consistent starting set of parameters and a common spinal target. For instance, in response to commands from external programmer 40, processor 50 may control stimulation generator 60 to deliver electrical neurostimulation to patient 36 via a first set of electrodes 48 that includes a first electrode that is a most midline electrode of electrodes 48 residing over a T9-T10 disk space of the patient and a second electrode immediately superior (i.e., above) the first electrode. Processor 50 controls stimulation generator 60 to deliver HD electrical neurostimulation to patient 36 via the first set of electrodes to provide pain relief therapy to patient 36.

As discussed above, if delivery of HD stimulation via the first set of electrodes is not effective in providing pain relief after a long enough period of time for HD stimulation to be effective in a first HD phase, stimulator 34 may subsequently deliver HD stimulation via a second set of electrodes during a second HD phase. Furthermore, if delivery of HD stimulation via the second set of electrodes is not effective in providing pain relief after a long enough period of time for HD stimulation to be effective, stimulator 34 may subsequently deliver LD stimulation to the patient during an LD phase.

Figure 3:
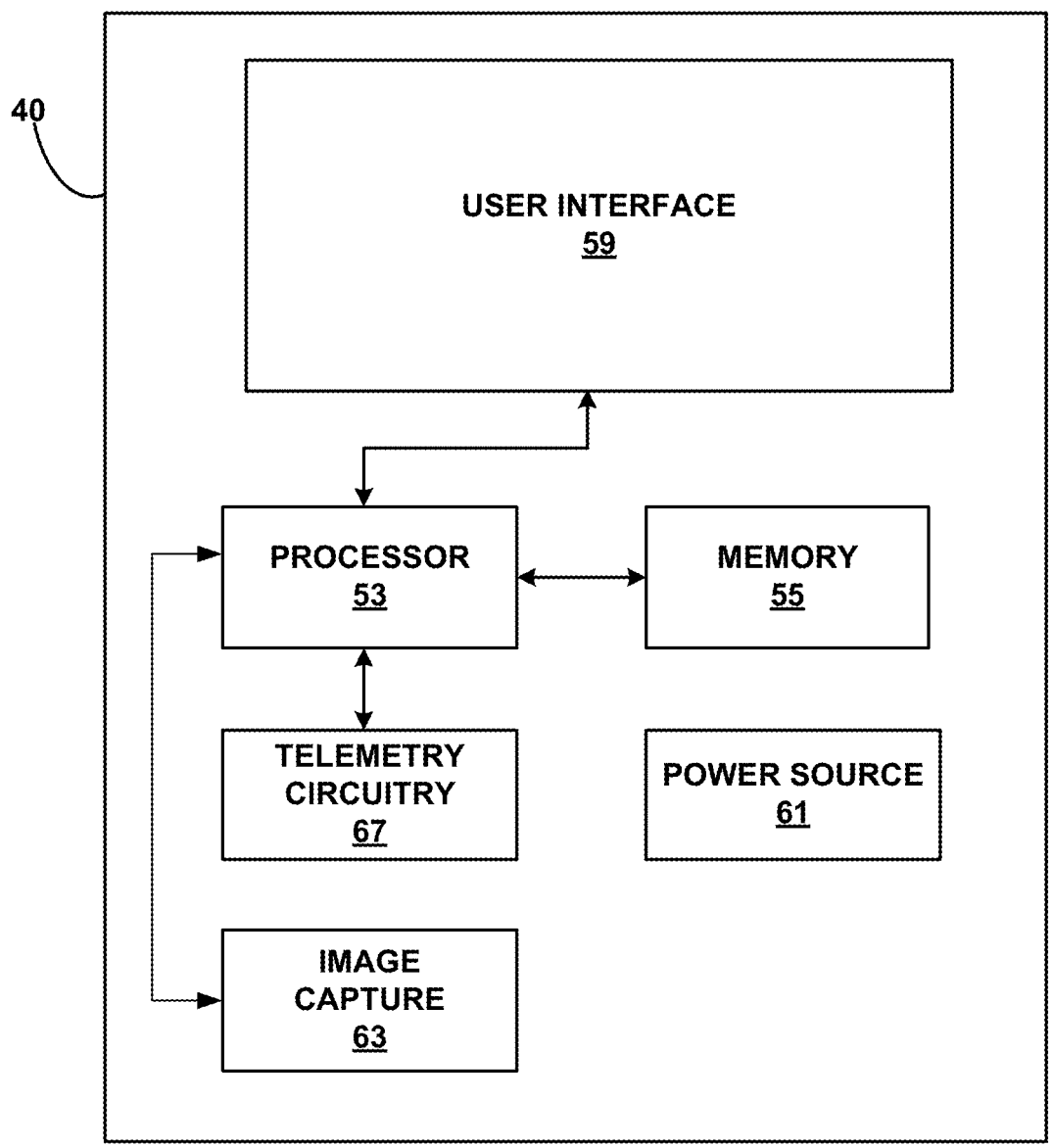
FIG. 3 is a functional block diagram illustrating various components of an external programmer for an implantable stimulator.

FIG. 3 is a functional block diagram illustrating various components of an external programmer 40 for an implantable stimulator 34. External programmer 40 of FIG. 3 may be a clinician programmer or a patient programmer. External programmer 40 includes processor 53, memory 55, telemetry module 67, user interface 59, and power source 61. In general, processor 53 controls user interface 59, stores and retrieves data to and from memory 55, and controls transmission of data with implantable stimulator 34 through telemetry module 67. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4, such as therapy delivery values.

In some examples, external programmer 40 includes an image capturing device 63. The image capturing device 63 may be built into the external programmer 40 or may be connected to the external programmer 40 via an interface using a wired or wireless connection. The processor 53 may control the image capturing device 63 to capture images as specified by the user of the external programmer 40. In some examples, image capturing device 63 may be a digital camera or web camera integrated with or coupled to programmer 40 to capture digital photographs of images presented on hardcopy media, such as film or paper, or a digital image display screen. Alternatively, the programmer may obtain the image electronically from an imaging device, a network storage server, a removable storage medium such as Flash memory, or other devices, directly or over a network.

A clinician or patient 36 interacts with user interface 59 in order to, for example, manually select, change, or modify programs, e.g., by adjusting voltage or current amplitude, adjusting pulse rate, adjusting pulse width, or selecting different electrode combinations or configurations, and may provide efficacy feedback, or view stimulation data. User interface 59 may include a screen and one or more input buttons that allow external programmer 40 to receive input from a user. The screen may be, for example, a liquid crystal display (LCD), plasma display, organic light emitting diode (OLED), electrophoretic displays, dot matrix display, or touch screen. The input buttons may include a touch pad, increase and decrease buttons, emergency shut off button, and other input media needed to control the stimulation therapy.

Using the techniques of this disclosure, a clinician or patient 36 may graphically define desired stimulation regions using interface 59, and may capture an image of the stimulated regions and the placement of the leads that stimulate the regions using the image capturing device 63. The clinician or patient 36 may utilize, for example, the user interface 59 to control the image capturing device 63 to obtain an image and to manipulate the image, as will be described in more detail below. In one example, the clinician or patient may utilize the image capturing device 63 directly to obtain the image.

Telemetry module 67 allows the transfer of data to and from stimulator 34. Telemetry module 67 may communicate automatically with stimulator 34 at a scheduled time or when the telemetry module detects the proximity of the stimulator. Alternatively, telemetry module 67 may communicate with stimulator 34 when signaled by a user through user interface 59. To support RF communication, telemetry module 44 may include appropriate electronic components, such as amplifiers, filters, mixers, encoders, decoders, and the like. In other examples, telemetry module 67 may employ other communication standards such as, for example, Bluetooth® and telemetry module 67 may include the appropriate Bluetooth® components.

Programmer 40 may communicate wirelessly with implantable stimulator 34 using, for example, RF communication or proximal inductive interaction or other communication standards such as, for example, Bluetooth®. This wireless communication is possible through the use of telemetry module 67 which may be coupled to an internal antenna or an external antenna. Telemetry module 67 may be similar to telemetry module 57 of implantable stimulator 34.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth® specification sets, infrared communication, e.g., based on the IrDA standard.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

According to the techniques of the disclosure, a clinician may, via external programmer 40, program stimulator 34 to perform any combination of the techniques of this disclosure.

Figure 4:
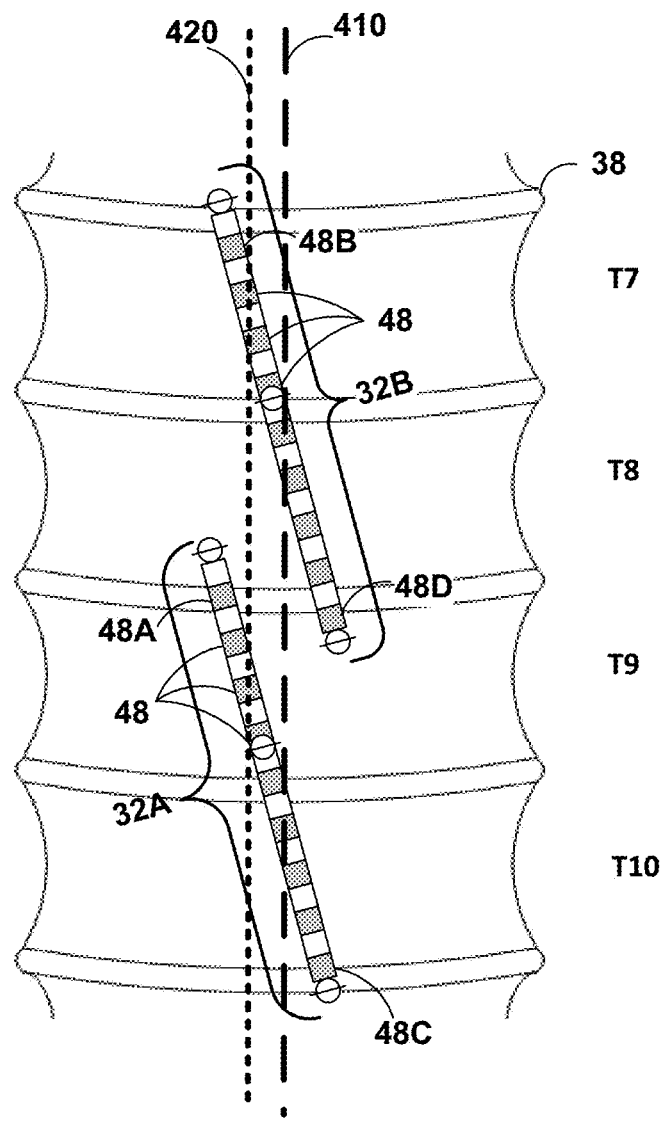
FIG. 4 is an illustration of example leads for delivering electrical neurostimulation in accordance with the techniques of the disclosure.

FIG. 4 is an illustration of example leads for delivering electrical neurostimulation in accordance with the techniques of the disclosure. The examples of FIG. 4 depicts implantable medical leads 32A, 32B (collectively leads 32) implanted along T7-T10 vertebrae of spine 38 of patient 36. Each of leads 32 further includes a plurality of electrodes 48.

A clinician may implant leads 32A and 32B substantially parallel to each other and at an angle relative to and across anatomical midline 410 of spinal cord 38 of patient 36. In some examples, the clinician implants leads 32A and 32B at an angle of 5-20 degrees relative to anatomical midline 410 of spinal cord 38 of patient 36. Such an implantation procedure as described herein may ensure that at least some of the electrodes are implanted on either side of physiological midline 420 of spinal cord 38. For example, an electrode combination including electrodes 48A of lead 32A and 48B of lead 32B are disposed on either side of physiological midline 420, and therefore may cause suppression of a pain sensation and/or paresthesia on both a left and a right lateral side of patient 36. However, an electrode combination including electrodes 48C of lead 32A and 48D of lead 32B does not include electrodes to the left lateral side of physiological midline 420. Thus, electrical stimulation via electrodes 48C and 48D may only cause suppression of a pain sensation and/or paresthesia on a right lateral side of patient 36. In some examples, by testing various combinations of electrodes 48, the clinician may determine a combination of electrodes that lies to both a left and a right lateral side of patient 36, and thereby determine the electrode combination that provides the greatest pain relief to the patient.

Figure 6:
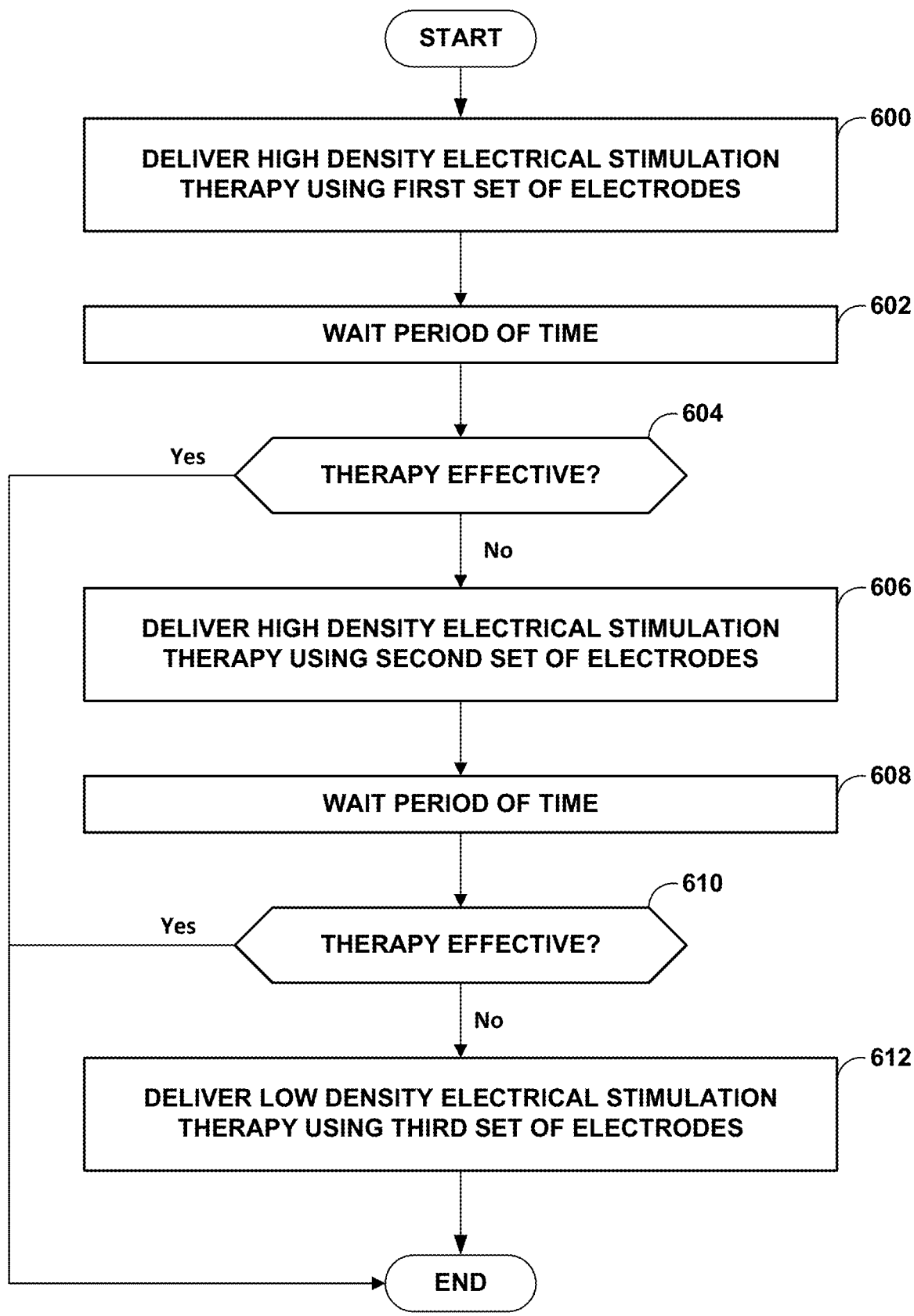
FIG. 6 is a flow diagram illustrating an example process for trialing high density electrical neurostimulation, in accordance with one or more techniques of this disclosure.

FIG. 6 is a flow diagram illustrating an example process for trialing high density electrical neurostimulation, in accordance with one or more techniques of this disclosure. Although FIG. 6 will be described with respect to processor 50 of implantable stimulator 34, similar processes would be performed by processor 53 and programmer 40.

Initially, implantable stimulator 34 may deliver high density electrical stimulation therapy using a first set of electrodes (600). For instance, implantable stimulator 34 may deliver electrical stimulation pulses with a duty cycle greater than a particular duty cycle threshold (e.g., 2%, 3%, 4%, 5%, 6%, 7%, etc.) using a first electrode that is implanted over a midline of a T9-T10 disk space of a patient and a second electrode that is immediately superior to the first electrode.

After waiting a period of time (602) (e.g., for the high density electrical stimulation to take effect), implantable stimulator 34 (or programmer 40) may determine whether or not the therapy is effective (604) (e.g., at reducing patient pain). Implantable stimulator 34 may continue to deliver the high density stimulation using the first set of electrodes during the period of time. If the therapy is effective ("yes" branch of 604), implantable stimulator 34 may continue to deliver high density electrical stimulation therapy using the first set of electrodes.

If the therapy is not effective ("no" branch of 604), implantable stimulator 34 may deliver high density electrical stimulation therapy using a second set of electrodes (606). For instance, implantable stimulator 34 may deliver electrical stimulation pulses with the particular duty cycle using the second electrode that is immediately superior to the first electrode and a third electrode that is immediately superior to the second electrode.

After waiting a period of time (608) (e.g., for the high density electrical stimulation to take effect), implantable stimulator 34 (or programmer 40) may determine whether or not the therapy is effective (610) (e.g., at reducing patient pain). Implantable stimulator 34 may continue to deliver the high density stimulation using the second set of electrodes during the period of time. If the therapy is effective ("yes" branch of 604), implantable stimulator 34 may continue to deliver high density electrical stimulation therapy using the second set of electrodes.

If the therapy is not effective ("no" branch of 604), implantable stimulator 34 may deliver low density electrical stimulation therapy using a third set of electrodes (612). For instance, implantable stimulator 34 may deliver electrical stimulation pulses with a duty cycle that is less than the particular duty cycle.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
   delivering, by an implantable medical device and during a first period of time, high density electrical neurostimulation therapy to a patient using a first set of electrodes of a plurality of electrodes;
   delivering, by the implantable medical device and during a second period of time, high density electrical neurostimulation therapy to the patient using a second set of electrodes of the plurality of electrodes; and
   delivering, by the implantable medical device and during a third period of time that is after the first and second periods of time, low density electrical neurostimulation therapy to the patient using a third set of electrodes of the plurality of electrodes,
   wherein delivering the high density electrical neurostimulation therapy comprises
   delivering pulses of electrical stimulation at a first duty cycle that is greater than or equal to a threshold duty cycle,
   wherein delivering the low density electrical neurostimulation therapy comprises delivering pulses of electrical stimulation at a second duty cycle that is less than the threshold duty cycle,
   wherein the first period of time, the second period of time, and the third period of time are non-overlapping, and
   wherein each of the first period of time and the second period of time is greater than or equal to 24 hours.

2. The method of claim 1, wherein the first set of electrodes comprises:
   a first electrode of the plurality of electrodes that is implanted over a midline of a T9-T10 disk space of the patient; and
   a second electrode of the plurality of electrodes that is immediately superior to the first electrode.

3. The method of claim 2, wherein the second set of electrodes comprises:
   the second electrode; and
   a third electrode of the plurality of electrodes that is immediately superior to the second electrode.

4. The method of claim 3, wherein:
   delivering the high density electrical neurostimulation therapy to the patient during the first period of time comprises delivering the high density electrical neurostimulation therapy to the patient using the first electrode as a cathode and the second electrode as an anode; and
   delivering the high density electrical neurostimulation therapy to the patient during the second period of time consists comprises the high density electrical neurostimulation therapy to the patient using the second electrode as a cathode and the third electrode as an anode.

5. The method of claim 1, wherein the first period of time and the second period of time are the same length.

6. The method of claim 1, wherein each of the first period of time and the second period of time is greater than or equal to 48 hours.

7. The method of claim 1, further comprising:
   adjusting, by the implantable medical device and based on user inputs, an amplitude of the high density electrical neurostimulation therapy.

8. The method of claim 1, wherein the threshold duty cycle is 5%.

9. The method of claim 1, wherein:
   delivering, using the first set of electrodes, the pulses of electrical stimulation at the first duty cycle comprises delivering, using the first set of electrodes, pulses of electrical stimulation at a particular frequency and with a particular pulse width; and
   delivering, using the second set of electrodes, the pulses of electrical stimulation at the first duty cycle comprises, delivering, using the second set of electrodes, pulses of electrical stimulation at the particular frequency and with the particular pulse width.

10. The method of claim 9, wherein the particular frequency is 1000 Hz, and wherein the particular pulse width is 90 micro-seconds.

11. The method of claim 1, wherein delivering, using the third set of electrodes, the pulses of electrical stimulation at the second duty cycle comprises delivering, using the third set of electrodes, pulses of electrical stimulation at a frequency that is less than the particular frequency and/or with a pulse width that is greater than the particular pulse width.

12. The method of claim 11, wherein the frequency of the high density electrical neurostimulation pulses is greater than 800 Hz, the frequency of the low density electrical neurostimulation pulses is less than 200 Hz, the pulse width of the high density electrical neurostimulation pulses is less than 100 microseconds, and/or the pulse width of the low density electrical neurostimulation pulses is greater than 200 microseconds.

13. The method of claim 1, further comprising:
   receiving an indication, prior to the second period of time, whether the delivery of the high density neurostimulation therapy during the first period of time was effective in treating pain experienced by the patient,
   wherein delivering the neurostimulation therapy during the second period of time comprises delivering the neurostimulation therapy during the second period of time in response to the indication that the delivery of the high density neurostimulation therapy during the first period of time was not effective in treating pain experienced by the patient.

14. A method comprising:
   delivering, by an implantable medical device and during a first period of time, high density electrical neurostimulation therapy to a patient using a first set of electrodes of a plurality of electrodes;
   receiving an indication whether the delivery of the high density neurostimulation therapy during the first period of time was effective in treating pain experienced by the patient; and
   in response to the indication that the delivery of the high density neurostimulation therapy during the first period of time was not effective in treating pain experienced by the patient, delivering, by the implantable medical device and during a second period of time that is after the first period of time, low density electrical neurostimulation therapy to the patient using a second set of electrodes of the plurality of electrodes,
   wherein delivering the high density electrical neurostimulation therapy comprises delivering pulses of electrical stimulation at a first duty cycle that is greater than or equal to a threshold duty cycle,
   wherein delivering the low density electrical neurostimulation therapy comprises delivering pulses of electrical stimulation at a second duty cycle that is less than the threshold duty cycle,
   wherein the first period of time, the second period of time, and the third period of time are non-overlapping, and wherein each of the first period of time and the second period of time is greater than or equal to 24 hours.

15. The method of claim 14, further comprising:
delivering, by the implantable medical device and during a third period of time that is between the first period of time and the second period of time, high density electrical neurostimulation therapy to the patient using a third set of electrodes of the plurality of electrodes.

16. An electrical neurostimulation therapy system comprising:
means for delivering, during a first period of time, high density electrical neurostimulation therapy to a patient using a first set of electrodes of a plurality of electrodes;
means for delivering, during a second period of time, high density electrical neurostimulation therapy to the patient using a second set of electrodes of the plurality of electrodes; and
means for delivering, during a third period of time that is after the first and second periods of time, low density electrical neurostimulation therapy to the patient using a third set of electrodes of the plurality of electrodes,
wherein delivering the high density electrical neurostimulation therapy comprises delivering pulses of electrical stimulation at a first duty cycle that is greater than or equal to a threshold duty cycle,
wherein delivering the low density electrical neurostimulation therapy comprises delivering pulses of electrical stimulation at a second duty cycle that is less than the threshold duty cycle,
wherein the first period of time, the second period of time, and the third period of time are non-overlapping, and
wherein each of the first period of time and the second period of time is greater than or equal to 24 hours.

* * * * *